United States Patent [19]

Rydell

[11] Patent Number: 4,784,636
[45] Date of Patent: Nov. 15, 1988

[54] BALLOON ATHEROECTOMY CATHETER

[75] Inventor: Mark A. Rydell, Golden Valley, Minn.

[73] Assignee: Schneider-Shiley (U.S.A.) Inc., Minneapolis, Minn.

[21] Appl. No.: 44,360

[22] Filed: Apr. 30, 1987

[51] Int. Cl.[4] ............................................. A61B 17/32
[52] U.S. Cl. ..................................... 604/22; 128/305; 128/755
[58] Field of Search ........ 128/304, 305, 344, 751–755; 604/22, 96

[56] References Cited

U.S. PATENT DOCUMENTS

| | | | |
|---|---|---|---|
| 4,273,128 | 6/1981 | Lary | 128/305 |
| 4,653,496 | 3/1987 | Bundy et al. | 128/305 |
| 4,669,469 | 6/1987 | Gifford, III et al. | 128/305 |
| 4,679,557 | 7/1987 | Opie et al. | 128/305 |
| 4,681,106 | 7/1987 | Kensey et al. | 128/305 |
| 4,690,140 | 9/1987 | Mecca | 128/305 |
| 4,696,667 | 9/1987 | Masch | 128/305 |

Primary Examiner—Dalton L. Truluck
Attorney, Agent, or Firm—Orrin M. Haugen; Thomas J. Nikolai; Frederick W. Niebuhr

[57] ABSTRACT

A catheter assembly especially designed for the performance of atherectomy procedures which includes a guide catheter having an inflatable balloon disposed on the distal end portion thereof, the guide catheter being dimensioned to receive in its lumen an elongated drive tube having an annular cutting tip affixed to the distal end thereof. A rotational drive mechanism is coupled to the drive tube at its proximal end for rotating same. Provision is also made in the drive mechanism for introducing fluid through the lumen of the guide catheter for inflating its balloon and for drawing a vacuum on the lumen of the drive tube for aspirating the treatment site. In use, the guide catheter with the drive tube and cutter head retracted is advanced up to the occlusion and then, the balloon is inflated to lock the distal end in place. Next, the cutter is rotated at high speed and advanced into the occlusion, while blood and any loose particulate matter is aspirated. The balloon is then deflated and advanced further into the lesion. These steps are repeated until the balloon is totally across the occlusion.

5 Claims, 1 Drawing Sheet

U.S. Patent  Nov. 15, 1988  4,784,636
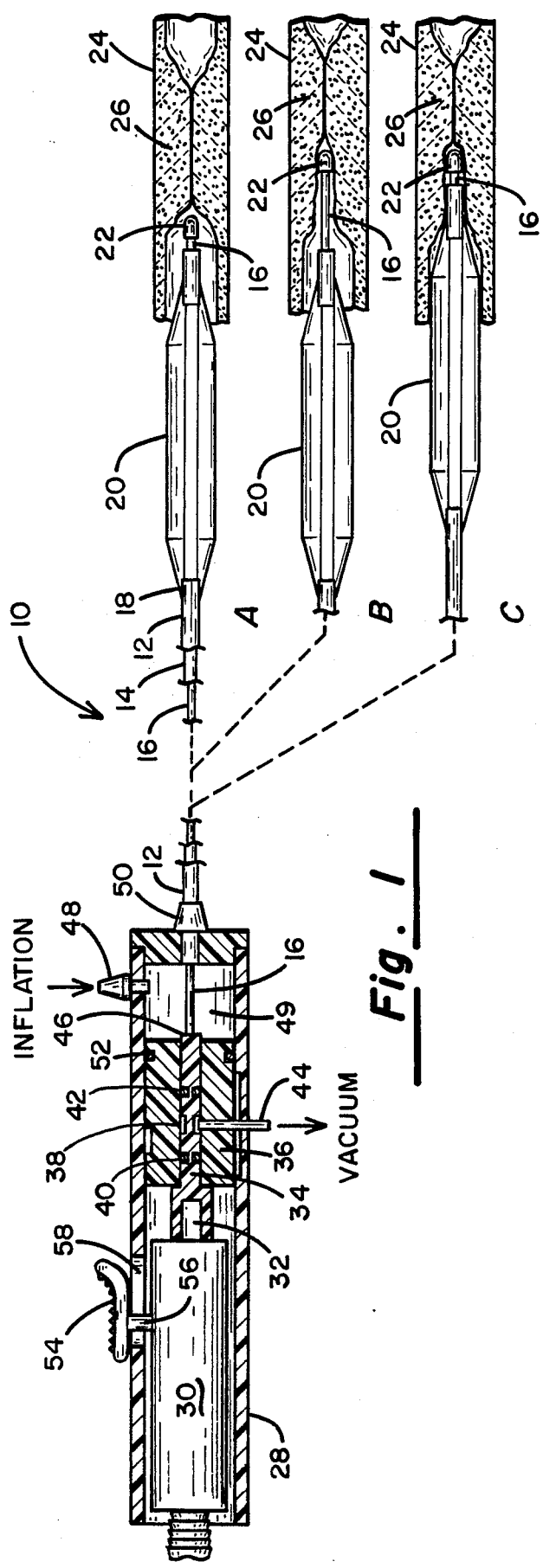
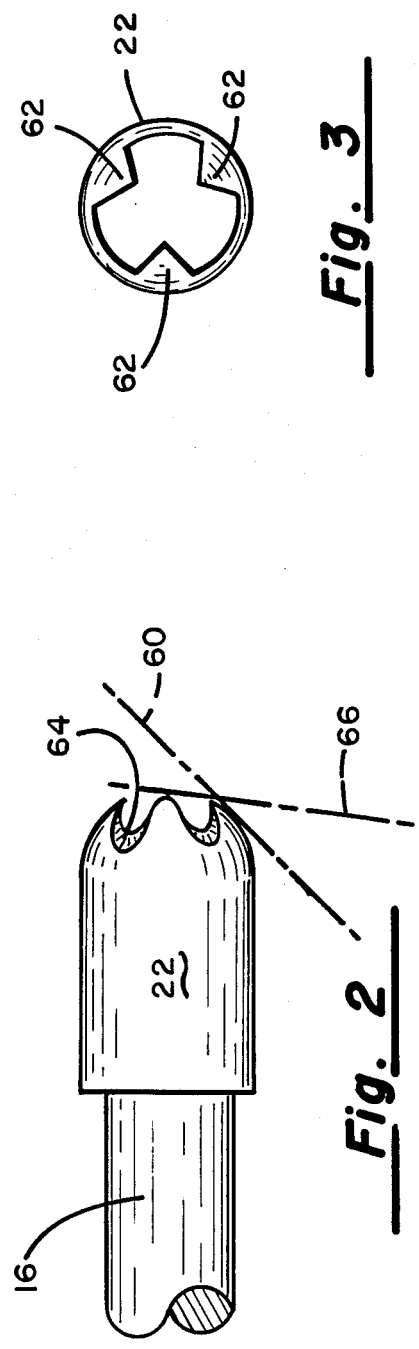

BALLOON ATHEROECTOMY CATHETER

BACKGROUND OF THE INVENTION

I. Field of the Invention:

This invention relates generally to intravascular catheters, and more particularly to the design of an atherectomy catheter useful in restoring patency to a blood vessel that is blocked or partially blocked by atheromas or other form of stenotic or thrombotic lesion.

II. Discussion of the Prior Art:

The build-up of atheromas or the formation of thrombi in a blood vessel can cause serious circulatory problems and when complete blockages occur, distal tissues may be deprived of oxygen and nutrients leading to death of those cells distally of the blockage. Thus, the formation of an atheroma in a coronary artery can lead to a coronary infarction, especially when the artery becomes so narrowed by the plaque build-up that a tiny clot or thrombus cannot pass. Similarly, an atheroma or other type of stenotic lesion in a peripheral vein or artery can have a corresponding affect on tissue and cells supplied by the blocked blood vessel.

The treatment of such a condition naturally depends upon the location or site of the blockage. In the case of a blocked or partially blocked coronary artery, it has been the practice to conduct open-heart surgery wherein the blocked vessel is by-passed with an autograft. Similarly, blood vessel shunts have been installed in other body areas as well. Such surgery, however, tends to be quite traumatic involving opening the patient's chest and pericardium in the case of coronary by-pass surgery or extensive excision and vessel replacement in the case of other peripheral blockages.

More recently, following the technique created to A. Grunzig, a balloon catheter may be used to restore patency to a blood vessel without extensive surgery. A catheter having a small inflatable balloon on its distal end may be routed through the vascular system to the site of the constriction or blockage and when the deflated balloon is appropriately positioned to span the blockage, a fluid may be introduced into the proximal end of the catheter to inflate the balloon to a sufficiently high pressure whereby the blockage may be spread open and patency restored.

As is pointed out in the Auth U.S. Pat. No. 4,445,509, there are certain deficiencies in the Grunzig procedure which render it ineffective in certain applications. For example, the blockage may be such that it is not possible to safely force the distal tip of the catheter through the blockage prior to the inflation of the balloon. In such a situation it would be desirable if one could safely "tunnel" through the blockage using an appropriate cutting tool. Once a passage has been formed during such tunneling operation, a balloon can be advanced into the occlusion until it is totally across it. Once so positioned, the balloon can then be inflated and the angioplasty procedure completed.

SUMMARY OF THE INVENTION

In accordance with the present invention, there is provided a balloon atherectomy catheter which is comprised of three concentrically disposed flexible plastic tubular members each providing a sufficient clearance between its respective outside diameter and the inside diameter of the adjacent tube whereby fluids may be perfused through the inter-tubular spaces. A inflation member (balloon) in the form of a thin biaxially oriented plastic film tube has its proximal end secured to the distal end of the outermost one of the three concentric tubes and its other (distal) end sealingly connected to the distal end of the intermediate tube. Then, by passing a fluid between the outer walls of the inner tube and the inner walls of the outer tube, the expander member may be inflated to a predetermined operating pressure.

The innermost tube has an annular cutter secured to its distal end, the end of the cutter having a predetermined profile so as to preferentially cut through a blockage without damaging the surrounding blood vessel tissue. Secured to the proximal end of the catheter assembly is a device which allows both rotational and translational motion to be imparted to the innermost tube. In addition, suitable valving is provided whereby a vacuum can be drawn through the lumen of the innermost tube for aspirating blood and any other debris which might be dislodged during the cutting of the atheroma or other blockage. Specifically, the proxima drive means and the inflation/suction means may comprise a tubular housing formed from a rigid plastic or other suitable material which contains a high velocity air motor of the type commonly used to power dental drills. The shaft of the air motor is coupled to the proximal end of the innermost catheter by way of a tubular sleeve which is mounted for rotational movement within a bearing which is also disposed in the tubular plastic housing. Suitable O-ring seals allow a negative pressure to be applied through the rotatable sleeve to the lumen of the inner tube. A thumb operated lever is used to displace the air motor and the valve-type coupler in the axial direction within the plastic housing, resulting in the ability to extend and retract the cutter from the end of the intermediate tube.

The tubular housing at the proximal end of the atherectomy catheter of this invention also includes an inflation port which communicates with the space between the inside wall of the outer tubular member and the outside wall of the intermediate tubular member whereby a fluid can be injected under pressure to inflate the expander member or, alternatively, to aspirate the inflation fluid thereby deflating the balloon.

In using the atherectomy catheter of the present invention, it may be entered into an appropriate incision and routed through the vascular system to the treatment site. Once the site is reached, a fluid may be injected to inflate the expander member to thereby stabilize the distal end portion of the catheter. Next, the air motor may be actuated to drive the innermost tube and the cutter on its end at a predetermined speed while axially advancing the center drive tube beyond the distal end of the intermediate tube and into the blockage. While the foregoing step is taking place, a vacuum may be applied to the proximal end of the drive tube for aspirating blood and tisuse matter through the lumen of the drive tube. Once a tunnel-like opening has been formed during such a cutting operation, the expander member may be deflated by aspirating the inflation fluid therefrom and once deflated, the entire catheter assembly may be advanced further into the occlusion, the balloon re-inflated, with the cutting aspiration and deflation steps being repeated until the tunnel expands completely through the blockage and the expander member completely bridges the lesion. Now, by once more expanding the expander member or balloon to its operating pressure, the atheroma or other blockage is pressed and spread, restoring patency to the previously occluded vessel.

The cutting of the atheroma and the subsequent restoration of the blood supply through the vessel has been found to result in an adsorption and significant reduction in the atheroma.

OBJECTS

It is accordingly a principal object of the present invention to provide an improved apparatus and technique for treating vascular atheromas.

Another object of the invention is to provide a catheter assembly including an outer balloon tipped guiding catheter and a central motor driven catheter having a cutting implement on its distal end for treating vessel blockages whereby patency can be restored.

Yet another object of the invention is to provide an atherectomy catheter in which the cutting end of the catheter may be positioned and stabilized within the blood vessel as the rotating cutter is advanced into the lesion.

Still another object of the invention is to provide a procedure utilizing a balloon tipped guiding catheter and a rotating cutter for treating blood vessel blockages.

It is still another object of the invention to provide a surgical implement for restoring patency to a blocked or partially blocked blood vessel, the implement including a motor driven cutter and a concentrically disposed balloon tipped catheter along with a proximally disposed device for allowing rotation of the cutter, aspiration of the treatment site, inflation of the balloon and longitudinal movement of the cutter relative to the balloon catheter.

These and other objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE DRAWINGS

FIG. 1A illustrates by means of a partially sectioned view the preferred embodiment of the invention with the cutter head shown in its retracted position;

FIG. 1B is a partial view showing the cutter in its extended position;

FIG. 1C is a partial view of the catheter of the present invention at a further step in the process;

FIG. 2 is a side view of the cutter tip; and

FIG. 3 is a distal end view of the cutter tip.

DESCRIPTION OF THE PREFERRED EMBODIMENT

Referring to FIG. 1A, the atherectomy catheter assembly of the present invention is indicated generally by numeral 10 and is seen to include three concentrically disposed elongated flexible tubular plastic members 12, 14 and 16. The outer tubular member 12 has a distal end portion 18 to which is sealingly affixed an inflatable expander member 20 which may preferably be formed from a thin biaxially oriented plastic such as polyethylene terephthalate (PET) or another suitable plastic. As can be seen in FIG. 1A, the distal end of the intermediate tubular member 14 projects beyond the distal end 18 of the outer tubular member 12 and the distal end of the expander 20 is sealed to the outer periphery thereof. As will be further explained, this will permit an inflation fluid to be injected through the lumen of the outer tube 12 and into the confines of the expander member 20. The expander 20 can subsequently be deflated by aspirating the inflation fluid out from the proximal end of the catheter assembly.

The innermost catheter 16, which is also referred to herein as the drive catheter, fits loosely within the lumen of the intermediate tube 14 and its distal end can be made to extend outwardly beyond the distal end of the intermediate catheter, all as shown in FIG. 1A. Attached to the distal end of the drive catheter 16 is an annular cutter 22 which is shown in greatly enlarged form in the views of FIGS. 2 and 3. Cutter 22 may be formed from either metal or plastic.

With continued reference to FIG. 1A, there is illustrated a blood vessel such as an artery or vein and it is indicated generally by numeral 24. The blood vessel is shown as being occluded by a fatty deposit (atheroma) 26.

For applying the rotational and translational motion to the drive tube 16 and for inflating and deflating the balloon 20 while aspirating blood and tissue deposits during the course of the atherectomy procedure, there is connected to the proximal end of the catheter a generally tubular housing 28 which is dimensioned to be conveniently grasped in the palm of the hand. Contained within the tubular housing 28 is a motor 30 which is preferably air driven but which alternatively may be electrically powered. The motor 30 has a shaft 32 which is keyed to a rotary union or valve member 34 contained within a valve housing 36. An annular groove 38 is formed in the rotatable union member 34 and disposed on opposed sides of the annular groove 38 are air seals 40 and 42 in the form of O-rings. A bore is formed through the side wall of the valve housing 36 and a fitting 44 fits within that bore for coupling it to a vacuum system (not shown).

The rotatable union member 34 is hollow and the annular recess 38 is ported to the hollow interior thereof by a radial bore (not shown). A coupler 46 is used to join the rotatable union 34 to the drive tube 16. Thus, by this arrangement, when the motor 30 is energized, the tubular drive member 16 is rotated within the lumen of the intermediate tube 14 and, simultaneously, a suction may be applied to the lumen of the drive tube 16 to draw blood and any tissue debris back to the proximal end of the assembly.

A fluid port 48 is also formed through the side wall of the tubular plastic housing member 28 and it communicates with a chamber 49. This chamber is adapted to be filled through port 48 with a suitable fluid such as saline solution and provides the means whereby the balloon or expander member 20 may be inflated. More particularly, the lumen of the outer tube 12 is open to the interior of the chamber 49 through compression fitting 50 and when the hydraulic pressure is appropriately increased, the saline solution flows into the expander member 20 to cause it to inflate to its maximum, predetermined outside diameter. By applying a negative pressure to the port 48 the inflation medium can be aspirated out from the proximal end of the outer tubular member 12 causing the expander member 20 to assume its low profile condition of being collapsed against the periphery of the intermediate tube 14. Again, an O-ring seal 52 is used to preclude the flow of liquid beyond the rotary union housing 36.

To effect translational or longitudinal movement of the cutter 22 relative to the distal end of the intermediate tube 14, there is provided on the housing 28 a thumb grip 54 having a stem 56 passing through an elongated slot 58 formed in the tubular housing 28. The stem 56 may be affixed to the motor assembly 30 which slidingly fits within the lumen of the tubular housing 28 or alternatively to the rotary union housing 36. Thus, by pushing on the thumb grip 54, the motor 30 and the rotary union 36 can be moved back and forth within the bore of the tubular housing 28.

Referring next to FIGS. 2 and 3, there is shown an enlarged view of the cutter tip 22. As can be seen, it comprises a generally annular member whose forward or distal end curves smoothly along a spherical locus so as to provide a relatively smooth surface to any obstruction which is somewhat tangent to the curve as represented by the line 60. Formed into the spherical face of the cutter are a series of cutting teeth as at 62 whose edges may be honed as at 64 in FIG. 2. When the cutter is made to abut a tissue surface at an angle of attack represented by line segment 66 which is more transversely oriented to the blood vessel 24 than is represented by the line 60, the teeth are effective to cut that tissue as the cutter 22 spins with the distal end of the drive tube 16.

OPERATION

FIGS. 1A, 1B and 1C are included to illustrate the preferred mode of operation of the atherectomy catheter of the present invention. As indicated in FIG. 1A, the catheter assembly with the cutter 22 retracted is advanced up to the occlusion 26 within the blood vesesl 24. At this point, saline or other suitable inflation fluid is injected through the port 48 into the chamber 49 and, thence, through the lumen of the outermost tube 12 to inflate the expander member 20. This action stabilizes the tip end of the catheter assembly and inhibits relative movement between the outer tubular member 12 and the blood vessel 24. Next, and as is represented by FIG. 1B, the motor 30 is energized to drive the cutter tube 16, and at the same time, the surgeon may, by pressing on the thumb grip 54, advance the rotating cutter tip into the lesion 26. While this procedure is taking place, a vacuum is preferably applied, via port 44 and the rotary valve member 34, to the lumen of the drive tube 16 whereby blood and other debris cut loose during the procedure is sucked back through the lumen of the drive tube and into a suitable receptacle (not shown).

Once a path has been cut into the lesion 26, the expander member 20 may be evacuated to collapse it to its smallest diameter and then by advancing the entire catheter assembly 10 further in the distal direction, the expander 20 is made to enter the previously cut opening in the lesion.

Following that, the expander may again be inflated and the steps repeated until such time as the balloon is made to pass completely through the occlusion to spread it open and to restore patency to the blood vessel 24.

Because of the manner in which the cutter head 22 is shaped, it is generally effective only against tissue surfaces extending somewhat normal to the direction of advance. Tangentially oriented tissue is not exposed to the cutting teeth, thus making it less likely that the endothelial lining of the blood vessel will be cut and abraded.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed is:

1. A method of conducting an atherectomy procedure comprising the steps of:
    (a) advancing a balloon tipped tubular guide catheter containing a coaxially disposed and axially moveable drive tube with a cutter member attached to its distal end through the vascular system to the site of the atheroma to be treated;
    (b) inflating the balloon on said tubular guide catheter;
    (c) rotating said drive tube and cutter at a predetermined speed while advancing said drive tube beyond the distal end of said guide catheter and into said atheroma;
    (d) during step (c), applying a vacuum to the proximal end of said drive tube for aspirating blood and tissue matter through the lumen of said drive tube;
    (e) deflating said balloon; and
    (f) repeating steps (a) through (e) until said balloon passes completely through the atheroma.

2. An atherectomy catheter assembly comprising:
    (a) a first, flexible tubular member of a predetermined outside and inside diameter having a proximal end, and distal end and a lumen extending from said proximal end to said distal end;
    (b) an inflatable expander member attached to said distal end of said first tubular member to be inflated by fluid passing through said lumen of said first tubular member;
    (c) a second tubular member having an outer diameter less than said predetermined inside diameter of said first tubular member, a proximal end, a distal end, and a lumen extending from said proximal end to said distal end of said second tubular member, said second tubular member being coaxially disposed within said lumen of said first tubular member with a predetermined clearance between said outer diameter of said second tubular member and said inside diameter of said first tubular member, allowing rotation and axial displacement of the distal end of said second tubular member beyond the distal end of said first tubular member;
    (d) a cutter member attached to said distal end of said second tubular member;
    (e) motor means coupled to said proximal end of said second tubular member for imparting rotation thereto within said lumen of said first tubular member;
    (f) means coupled to said proximal end of said first tubular member for directing fluid through said lumen of said first tubular member to inflate and deflate said expander member;
    (g) means for applying a negative pressure to said lumen of said second tubular member at the proximal end portion thereof; and
    (h) means located at said proximal end of said second tubular member for axially extending and retracting said distal end of said second tubular and said cutter member from said distal end of said first tubular member as said second tubular member is being rotated by said motor means.

3. The atherectomy catheter as in claim 2 wherein said cutter member is generally annular in shape and is serrated on a working edge thereof.

4. The atherectomy catheter as in claim 3 wherein the serrations only effectively engage a surface for cutting when said surface is at least at a predetermined minimum angle to the longitudinal axis of said cutter member.

5. The atherectomy catheter as in claim 2 and further including an intermediate tubular member coaxially disposed relative to said first and second tubular members and arranged such that the inflation fluid passes through the space between said first and said intermediate tubular members.

* * * * *

UNITED STATES PATENT AND TRADEMARK OFFICE
CERTIFICATE OF CORRECTION

PATENT NO. : 4,784,636
DATED : November 15, 1988
INVENTOR(S) : Mark A. Rydell

It is certified that error appears in the above-identified patent and that said Letters Patent is hereby corrected as shown below:

Title page, at [54] change "ATHEROECTOMY" to -- ATHERECTOMY --.

Claim 1, column 6, line 22, after "cutter" insert -- member --.

Claim 2, column 6, line 35, change "and" (first occurrence) to -- a --.

Claim 2, column 7, line 1, after "tubular" insert -- member --.

Signed and Sealed this

Twenty-eighth Day of March, 1989

Attest:

DONALD J. QUIGG

Attesting Officer

Commissioner of Patents and Trademarks